(12) United States Patent
Beckman et al.

(10) Patent No.: US 7,465,279 B2
(45) Date of Patent: Dec. 16, 2008

(54) MARKER DEVICE AND METHOD OF DEPLOYING A CAVITY MARKER USING A SURGICAL BIOPSY DEVICE

(75) Inventors: Andrew T. Beckman, Cincinnati, OH (US); Rick D. Applegate, Florence, KY (US); Michael E. Boehm, Cincinnati, OH (US); William A. Garrison, Springdale, OH (US); Douglas N. Ladd, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 226 days.

(21) Appl. No.: 10/815,004

(22) Filed: Mar. 31, 2004

(65) Prior Publication Data

US 2005/0228311 A1    Oct. 13, 2005

(51) Int. Cl.
*A61B 10/00* (2006.01)
(52) U.S. Cl. .................. 600/566; 600/567; 606/170
(58) Field of Classification Search ......... 600/562–572; 606/167, 170, 180
See application file for complete search history.

(56) References Cited

U.S. PATENT DOCUMENTS

| | | | | |
|---|---|---|---|---|
| 3,744,493 A | * | 7/1973 | Booher et al. | 604/62 |
| 4,007,732 A | * | 2/1977 | Kvavle et al. | 600/567 |
| 4,774,948 A | * | 10/1988 | Markham | 606/185 |
| 4,900,304 A | * | 2/1990 | Fujioka et al. | 604/60 |
| 5,286,257 A | * | 2/1994 | Fischer | 604/82 |
| 5,526,822 A | | 6/1996 | Burbank et al. | |
| 5,649,547 A | | 7/1997 | Ritchart et al. | |
| 5,718,237 A | * | 2/1998 | Haaga | 600/564 |
| 5,769,086 A | | 6/1998 | Ritchart et al. | |
| 5,775,333 A | | 7/1998 | Burbank et al. | |
| 5,810,806 A | | 9/1998 | Ritchart et al. | |
| 5,902,310 A | | 5/1999 | Foerster et al. | |
| 5,913,857 A | | 6/1999 | Ritchart et al. | |
| 5,922,002 A | | 7/1999 | Yoon | |
| 5,928,164 A | | 7/1999 | Burbank et al. | |
| 5,941,890 A | | 8/1999 | Voegele et al. | |
| 5,944,673 A | | 8/1999 | Gregoire et al. | |
| 5,964,716 A | | 10/1999 | Gregoire et al. | |

(Continued)

FOREIGN PATENT DOCUMENTS

EP    1 249 209    10/2002

(Continued)

OTHER PUBLICATIONS

Ethicon Endo-Surgery, Inc., Mammotome® HH (2000), Johnson & Johnson, pp. 1-7.

(Continued)

*Primary Examiner*—Max Hindenburg
*Assistant Examiner*—Rene Towa

(57) ABSTRACT

A biopsy marker introduction assembly is configured for introduction through a specimen retrieval recess into a probe cutter lumen of a handheld breast biopsy handle. Advancing the cutter causes an extending deployment rod to distally translate within an introducer tube of the introduction assembly, pushing a biopsy marker out of a distal end of the probe at a surgical biopsy site. Thereby, the surgeon is able to position the probe and effect deployment of the marker even if using the other hand to position an imaging device such as an ultrasonic transceiver.

20 Claims, 5 Drawing Sheets

U.S. PATENT DOCUMENTS

| | | | |
|---|---|---|---|
| 5,980,469 A | 11/1999 | Burbank et al. | |
| 6,007,497 A | 12/1999 | Huitema | |
| 6,017,316 A | 1/2000 | Ritchart et al. | |
| 6,077,230 A | 6/2000 | Gregoire et al. | |
| 6,083,237 A | 7/2000 | Huitema | |
| 6,085,749 A | 7/2000 | Wardle et al. | |
| 6,086,544 A | 7/2000 | Hibner et al. | |
| 6,120,462 A | 9/2000 | Hibner et al. | |
| 6,162,187 A | 12/2000 | Buzzard et al. | |
| 6,220,248 B1 | 4/2001 | Voegele et al. | |
| 6,228,055 B1 | 5/2001 | Foerster et al. | |
| 6,231,522 B1 | 5/2001 | Voegele et al. | |
| 6,234,177 B1 * | 5/2001 | Barsch | 128/897 |
| 6,241,687 B1 | 6/2001 | Voegele et al. | |
| 6,261,302 B1 | 7/2001 | Voegele et al. | |
| 6,273,862 B1 | 8/2001 | Privitera et al. | |
| 6,371,904 B1 * | 4/2002 | Sirimanne et al. | 600/3 |
| 6,375,634 B1 * | 4/2002 | Carroll | 604/19 |
| 6,394,965 B1 | 5/2002 | Klein | |
| 6,428,486 B2 | 8/2002 | Ritchart et al. | |
| 6,428,487 B1 | 8/2002 | Burdorff et al. | |
| 6,432,064 B1 | 8/2002 | Hibner et al. | |
| 6,432,065 B1 | 8/2002 | Burdorff et al. | |
| 6,436,068 B1 * | 8/2002 | Bardy | 604/57 |
| 6,488,030 B1 | 12/2002 | Wardle et al. | |
| 6,554,760 B2 | 4/2003 | Lamoureux et al. | |
| 6,557,196 B2 | 5/2003 | Falbo, Sr. et al. | |
| 6,558,407 B1 | 5/2003 | Ivanko et al. | |
| 6,560,310 B2 | 5/2003 | Stark | |
| 6,567,689 B2 | 5/2003 | Burbank et al. | |
| 6,602,204 B2 * | 8/2003 | Dubrul et al. | 600/567 |
| 6,638,235 B2 * | 10/2003 | Miller et al. | 600/566 |
| 6,648,811 B2 * | 11/2003 | Sierocuk et al. | 600/7 |
| 6,662,041 B2 | 12/2003 | Burbank et al. | |
| 2002/0082517 A1 | 6/2002 | Klein | |
| 2002/0161298 A1 | 10/2002 | Burbank et al. | |
| 2003/0050571 A1 | 3/2003 | Zarins et al. | |
| 2004/0030262 A1 * | 2/2004 | Fisher et al. | 600/564 |

FOREIGN PATENT DOCUMENTS

| | | |
|---|---|---|
| WO | WO 00 38579 | 7/2000 |
| WO | WO 02 13876 | 2/2002 |
| WO | WO 02 078560 | 10/2002 |
| WO | WO 03 022133 | 3/2003 |
| WO | WO 03 034894 | 4/2003 |

OTHER PUBLICATIONS

Ethicon Endo-Surgery, Inc., MicroMark™ II (1999), Johnson & Johnson, pp. 1-7.

Arternis Medical, Inc., MammoMark™ Biopsy Site Marker (2001), pp. 1-6.

SenoRx Inc., SenoRx Gel Mark™ Biopsy Site Marker ((2001), pp. 1-4.

* cited by examiner

MARKER DEVICE AND METHOD OF DEPLOYING A CAVITY MARKER USING A SURGICAL BIOPSY DEVICE

FIELD OF THE INVENTION

The present invention relates, in general, to an applier for delivering and deploying a marker for implantation in tissue of a surgical patient, and more particularly, to such an applier for delivering and deploying an implantable biopsy marker for defining specific locations in human tissue during a biopsy procedure, especially in a human breast.

BACKGROUND OF THE INVENTION

One in nine American women will develop breast cancer in their lifetime. It is the leading cause of cancer deaths in women 40-55 years of age and the second leading cause of cancer deaths in women overall. Breast cancer will be diagnosed in approximately one in eight women in their lifetime, and one in 30 will die of this disease. Breast cancer does occur in males, but is much less common. Biopsy requests stem from a screening process generally performed via a physical examination (palpable) and/or mammogram (non-palpable). A biopsy is indicated if suspicious tissue is detected. Five out of six biopsies performed return benign indications.

It is desirable and often necessary to perform procedures for detecting, sampling, and testing lesions and other abnormalities in the tissue of humans and other animals, particularly in the diagnosis and treatment of patients with cancerous tumors, pre-malignant conditions and other diseases or disorders. Typically, in the case of cancer, when a physician establishes by means of known procedures (i.e. palpation, x-ray, magnetic resonance imaging (MRI), or ultrasound imaging) that suspicious circumstances exist, a biopsy is performed to determine whether the cells are cancerous. Biopsy may be an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In the FNA biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination, which may be done via a frozen section or paraffin section. The chief difference between FNA and core biopsy is the size of the tissue sample taken. An imaging system having spectroscopic capabilities, such as the stereotactic guidance system, is employed to guide the extraction instrument to the lesion.

A significant advance in core biopsies in a diagnostic imaging modality such as X-ray, MRI, ultrasonic, etc. have been facilitated by a hand-held biopsy device, such as described in U.S. Pat. No. 6,086,544, the disclosure of which is hereby incorporated by reference in its entirety. Being handheld, this generally known "MAMMOTOME" breast biopsy system creates a less intimidating and more-comfortable arrangement for the patient with minimal procedure preparation time as compared to a tabletop fixed biopsy device. The procedure may be completed in less than an hour in a doctor's office or on an outpatient basis under a local anesthetic and requires no surgery or stitches. It allows the patient to lie comfortably on her back.

A probe need only be inserted once into the patient's breast via a small incision. Once inserted and positioned via imaging (e.g., ultrasonic, MRI), the needlelike probe can collect multiple samples by means of vacuum aspiration and an internal rotating cutter. The vacuum draws the sample into the probe aperture within reach of the cutter. From there, tissue samples can be obtained in and around the targeted area. Even though the incision is smaller, these samples can be eight times the weight of samples obtained with traditional spring-loaded biopsy equipment.

It should be appreciated that a generally known vacuum assisted breast biopsy system described above has incorporated an onboard microprocessor to automate the sampling process. A positioning sensor allows the color touch-screen monitor to reflect the exact position of the cutting tip. An easy-to-follow graphical user interface gives surgeons maximum control over the location from which the biopsy sample is taken. A two-motor cutting drive system self-contained in the base unit and connected to a lightweight handpiece eliminates the need to table-mount the cutter assembly. Lightweight, flexible cables connect the base to the disposable handpiece. This handheld unit, which incorporates cutter position sensors, allows physicians to place the sampling probe accurately and obtain larger samples of suspect tissue.

The cutting drive system includes direct feedback control of both cutter translational and rotational speeds. When either the translational speed or rotational speed is not at the desired rate due to increased or decreased loading on the system, the control feature modifies the power to the motor. This allows the speeds to remain near their desired levels, enabling maximum control throughout the procedure. The cutter can sample both palpable and nonpalpable lesions, including spiculated masses, asymmetric densities, multifocal disease, and diffuse tissue.

In addition, the handheld cutting probe includes ergonomic features to allow for easy manipulation and procedure control such as a soft-touch finger-control keypad. Precise position control lets the cutter close the aperture through which the sample enters without bottoming out at the end of the probe. Good position control (e.g., within 0.001 in.) enables the minimization of the length of the cushion, or "dead zone," at the end of the probe. Incision of the tissue and completion of the sampling as directed is achieved without causing damage to healthy surrounding tissue.

This hand-held biopsy device is capable of rapidly taking a number of biopsy samples, assisted by a vacuum capability that draws tissue into proximity with a cutter. A computer-controlled vacuum system enables the vacuum to cycle on and off, and optimizes the vacuum in accord with the cutter activity. The vacuum retrieval system allows the caregiver to take multiple samples of a lesion while the needle probe remains in the breast. Moreover, large enough samples are obtainable, avoiding dry taps, or the inability to obtain an adequately sized sample of the suspect tissue, a common problem associated with other breast biopsy systems. Moreover, the hand-held biopsy device may further completely remove suspicious material as a therapeutic treatment for suspicious lesions.

With this ability to completely remove a lesion, however, comes a desire to mark this location for later reference, such as for further treatments or later diagnostic follow-up. To that end, an applier for an implantable surgical marker is advantageously used in conjunction with a hand-held biopsy device, such as described in U.S. Pat. No. 6,261,302, the disclosure of which is hereby incorporated by reference in its entirety. After a last specimen is retrieved from a probe of the hand-held biopsy device, the cutter is withdrawn so that an open lumen is presented between a specimen collection bowl and a distal aperture of the probe. A flexible introducer of the marker applier is inserted through the lumen and then the marker is released at the desired location by depressing a button on the marker applier.

While this technique accomplishes the desired end, it would be desirable to simplify the procedure. For instance, when using ultrasonic imaging to position the probe of the biopsy device, the surgeon typically has to hold an ultrasonic transceiver with one hand. The other hand directs the biopsy device to the desired location and controls the taking of samples. Then a third hand is needed to actuate the marker applier. It would be desirable that a two-hand procedure would be adequate while maintaining the efficiency and convenience of using a handheld biopsy system.

In addition, it would be desirable to have the same degree of control and repeatability in marker placement that is available in taking the tissue samples themselves. Generally-known marker placement devices, such as the MICROMARK II device described above, relies upon the user to insert its distal end fully through the open needle of the biopsy device. Actuating the marker placement device in some instances may fail to deploy the marker from the biopsy probe, however.

Consequently, a significant need exists for an improved approach to placing a biopsy marker with the aid of a biopsy instrument.

BRIEF SUMMARY OF THE INVENTION

The invention overcomes the above-noted and other deficiencies of the prior art by providing a marker introducing assembly that advantageously conforms to a biopsy probe and is actuated by a cutter of a biopsy handle to deploy a biopsy marker out of a distal end of the biopsy probe. Thereby, a surgeon may advantageously position the biopsy probe to a desired surgical site and actuate a cutter control to deploy the marker while having another hand free to perform other functions such as positioning an ultrasonic transceiver for imaging the biopsy probe.

In one aspect of the invention, a biopsy introducing assembly includes an alignment feature that confirms a fully seated and oriented placement into the biopsy probe so that advancement of the cutter of the biopsy handle will achieve full travel without bottoming out to reliably deploy the marker.

In another aspect of the invention, a biopsy system and method alters a direct feedback control of the cutter of the biopsy handle to a desired translation distance appropriate for the marker introducing assembly to reliably deploy the marker without bottoming out a plunger therein that communicates between the marker and the cutter. In addition to translation distance control, rate of translation and disabling cutter revolution may be included. Thereby, the surgeon is able to use biopsy controls in a familiar manner for deploying the marker as is used in taking the biopsy samples.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
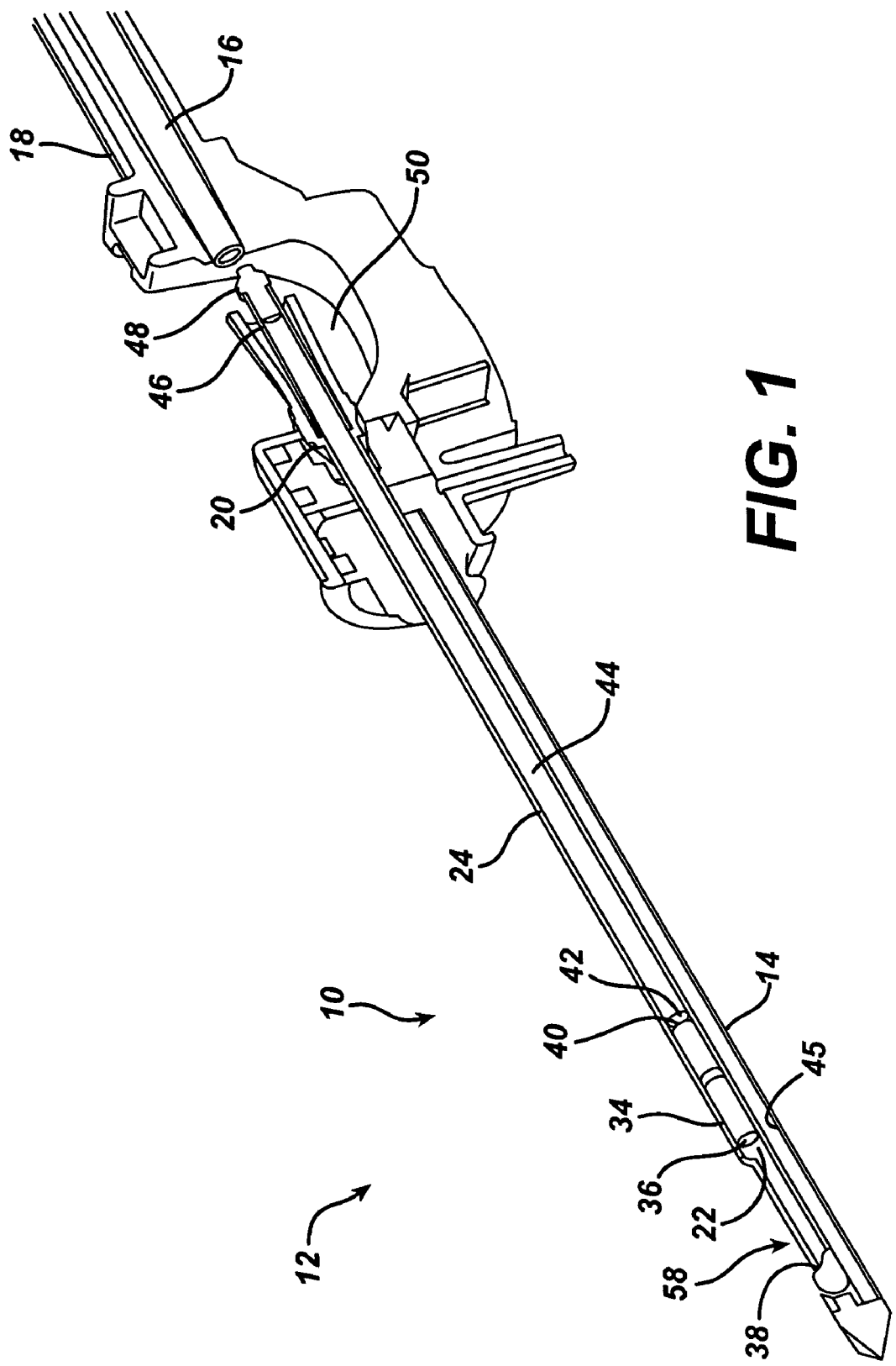
FIG. 1 is a left side elevation view with a left half cut-away of a biopsy system with a cutter of a biopsy handle retracted allowing placement of a biopsy marker introduction assembly into a biopsy probe.

Turning to the Drawings, wherein like numerals refer to like components throughout the several views, in FIG. 1, a breast biopsy handle 10 of a biopsy system 12, a minimally invasive device, is used under local anesthetic and ultrasound guidance to collect multiple biopsy samples with a single insertion of a probe 14 into the breast of a patient. After which, a cutter 16 is retracted proximally in a housing 18 of the biopsy handle 10 to expose a distally opening entry cone 20 of a cutter lumen 22 of the probe 12. The surgeon may then insert and seat a biopsy marker introduction assembly 24, which is shown separately in FIG. 2.

Figure 2:
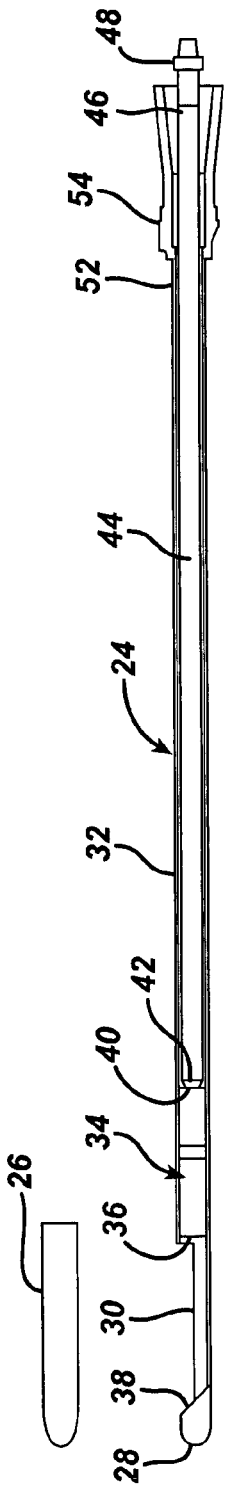
FIG. 2 is a left side elevation view in cross section of the biopsy marker introduction assembly of FIG. 1.

Also shown in FIG. 2 is a Mylar sealing cap 26 that has been removed just prior to use from a distal end 28 of the introduction assembly 24 to expose a laterally disposed deployment opening 30 in an introducer tube 32. A marker 34 is positioned inside of the introducer tube 32 proximal to the deployment opening 30 that has sufficient length to allow the marker 34 to be laterally expelled when a distal end 36 of the marker 34 ramps against an angled surface 38 at the distal end 28 of the introduction assembly 24. Thus, a proximal end 40 of the marker 34 resides approximately twice the length (2×) of the marker 34 from the angled surface 38 when in its initial state as depicted. Abutting this proximal end 40 is a marker pusher, depicted as a plunger tip 42 of a marker deployment rod 44 that longitudinally translates within the introducer tube 32. The plunger tip 42 in some applications dynamically seals to the interior of the introducer tube 32 to form a sterile environment for the marker 34 and to pneumatically assist in deploying the marker 34. For instance, the plunger tip 42 may push air toward the marker 40 as a syringe, which may advantageously reduce the amount of travel required for the cutter 16. Alternatively or in assistance thereof, a vacuum lumen 45 in the probe 14 may provide vacuum assist to draw the plunger tip 42 and bleed any excess pressure from the surgical site.

A proximal end 46 of the marker deployment rod 44 terminates in a cutter seat 48 that extends proximally beyond the entry cone 20 of the cutter lumen 22 a sufficient distance to provide full travel of the marker deployment rod 44 yet fit within a specimen retrieval recess 50 formed within the housing 18 of the biopsy handle 10. The cutter seat 48 has a greater lateral diameter than the tube-shaped cutter 16 to ensure contact. Since the cutter 16 closely fits the inner diameter of the cutter lumen 22, the cutter seat 48 reaches full travel at the entry cone 20.

Figure 3:
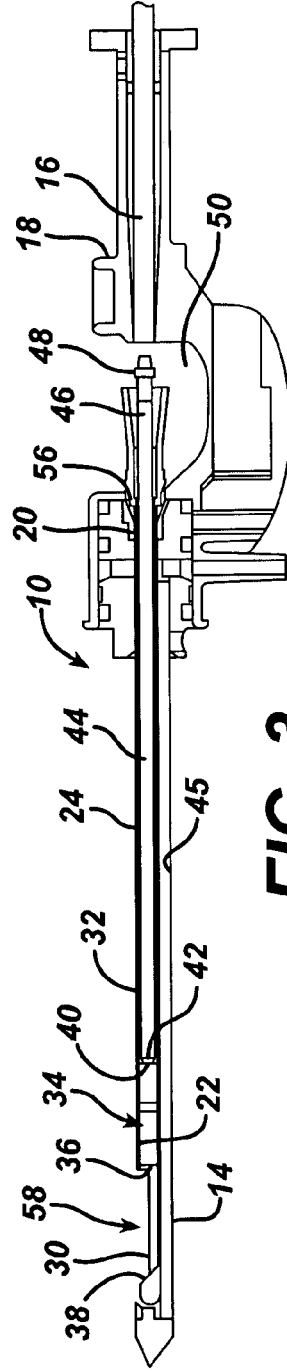
FIG. 3 is a left side elevation view in cross section of the biopsy marker introduction assembly seated in the biopsy probe of FIG. 1.

With reference to FIGS. 2-3, a funnel 50 flared proximally and attached to a proximal end 52 of the introducer tube 32 encompasses the cutter seat 48 and the portion of the marker deployment rod 44 that extends proximal to the entry cone 20. The funnel 50 advantageously includes an alignment feature, such as a transversely extending key 54, that mates with a corresponding alignment feature in the biopsy probe 14, such as a proximally opened recess 56. These alignment features 54, 56 ensure that the marker introduction assembly 30 is correctly rotated to present its deployment opening 30 to a specimen opening 58 of the probe 14. In addition, visual and tactile confirmation is given that the introduction assembly 24 is fully inserted into the probe 14 so that reliable deployment of the marker 34 may be achieved.

Figure 4:
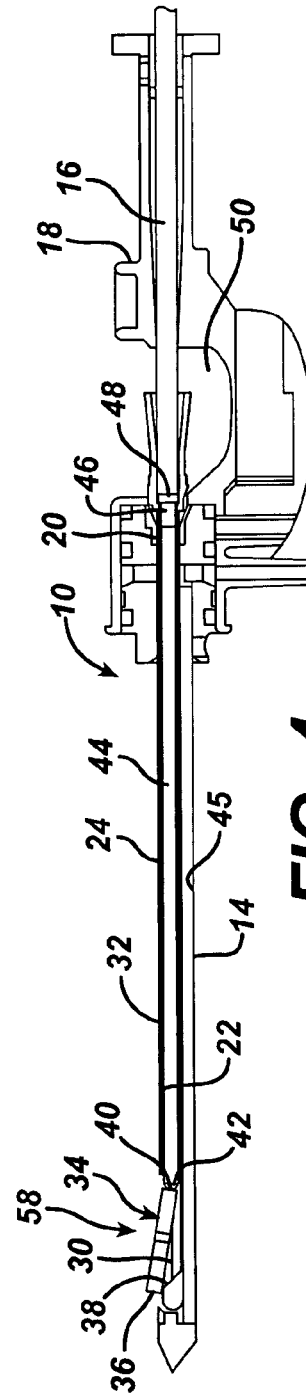
FIG. 4 is a left side elevation view in cross section with the cutter advanced to drive a plunger through an introducer tube to deploy the marker out of the biopsy probe of the biopsy handle of FIG. 1.

In FIG. 4, the cutter 16 has been advanced, distally translating the deployment rod 44 to deploy the marker 34. Then the probe 14 may be withdrawn leaving the marker 34 behind. In some applications, the existing controls of the biopsy system 12 may be used to achieve deployment as depicted in FIG. 4. Thus, the cutter seat 48 may advantageously resist damage from a cutter 16 that is rotating (e.g., hardened surface, low friction surface, or configured to be rotated by the cutter). The surgeon would command forward translation of the cutter until visually confirming full travel or the cutter is prevented from further travel by the cutter seat 48 engaging introducer tube 32.

Figure 6:
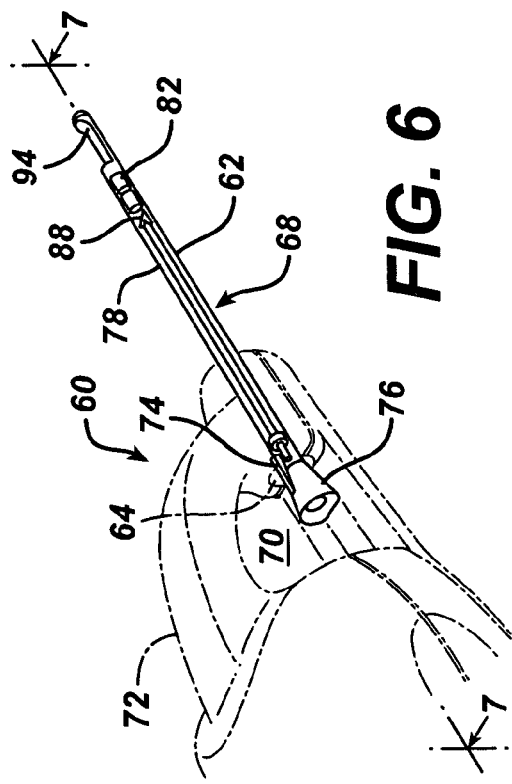
FIG. 6 is a perspective view of the handheld breast biopsy device of FIG. 5 with the flexible marker introduction assembly further inserted.
Figure 5:
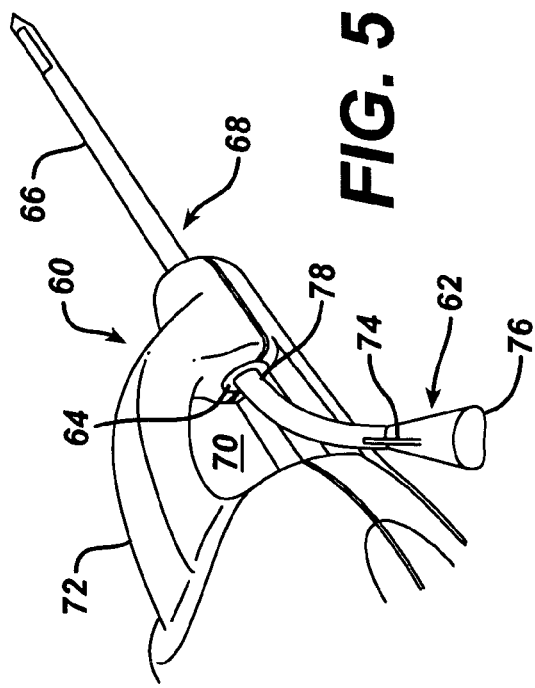
FIG. 5 is a perspective view of a handheld breast biopsy device in phantom with a flexible marker introduction assembly being inserted.

In FIGS. 1-4, the breast biopsy handle 10 depicted is similar to sterotactic devices attached to a tabletop. A handheld MRI-compatible biopsy device 60 is depicted in phantom in FIGS. 5-6 for use with a marker introduction assembly 62. In some applications, access to an entry cone 64 of a cutter lumen 66 of a probe 68 may be constrained by the shape of a specimen retrieval recess 70 formed in a handle 72 of the handheld breast biopsy device 60. Consequently, portions of the marker introduction assembly 62 are formed of a sufficiently flexible material, as depicted in FIG. 5, to be bent during insertion into the biopsy handle 70. In FIGS. 5-6, an alignment key 74 along the top of a funnel 76 rotationally and longitudinally orients an attached introducer tube 78 within the cutter lumen 66 of the probe 68. The introducer tube 78 is sufficiently thin to allow advancement of a cutter 80 (depicted in FIGS. 8-11) as desired within the cutter lumen 66 without binding. This has an added advantage of thus being usable in specimen retrieval recesses 70 that are not at least twice the length of a marker 82 or when it is otherwise desirable to advance the cutter 80 more fully during deployment of the marker 82.

Figure 7:
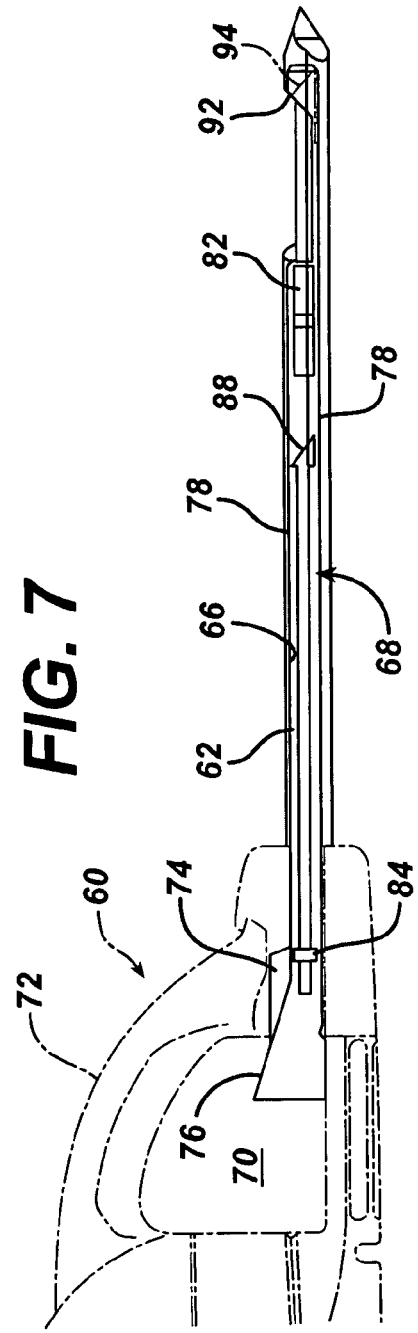
FIG. 7 is a right-side elevation view of the handheld breast biopsy device taken in longitudinal cross section along lines 7-7 of FIG. 6.
Figure 8:
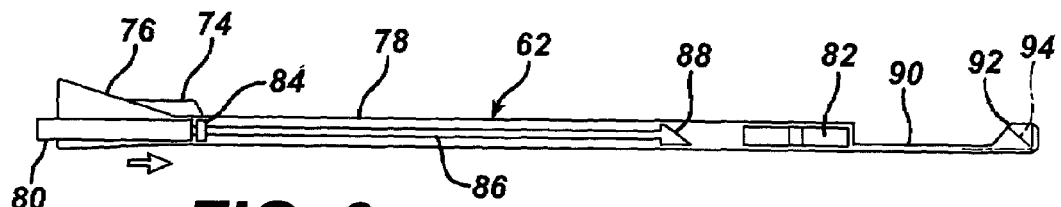
FIGS. 8-11 are right side elevation views of a cutter of the handheld breast biopsy device and the marker introduction assembly taken in longitudinal cross section along lines 7-7 of FIG. 6 depicting a sequence respectively of the cutter engaging the pusher, the cutter advanced to expose a marker in a specimen opening of the probe, the cutter advanced to ramp a distal end of the marker against an angled surface of the assembly, and the cutter advanced to fully deploy the marker by underrunning a driver tip of the pusher.
Figure 9:
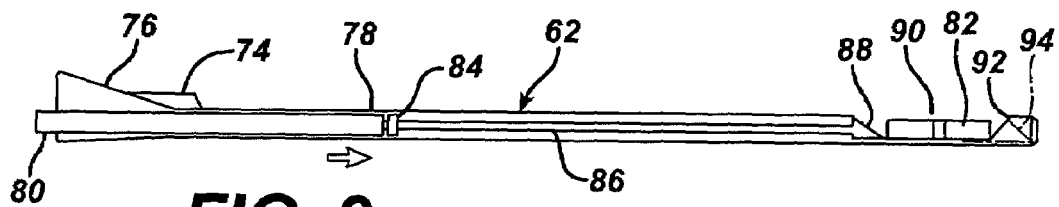
Figure 10:
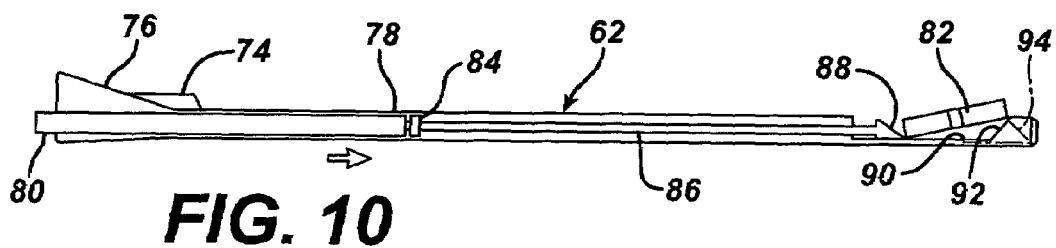
Figure 11:
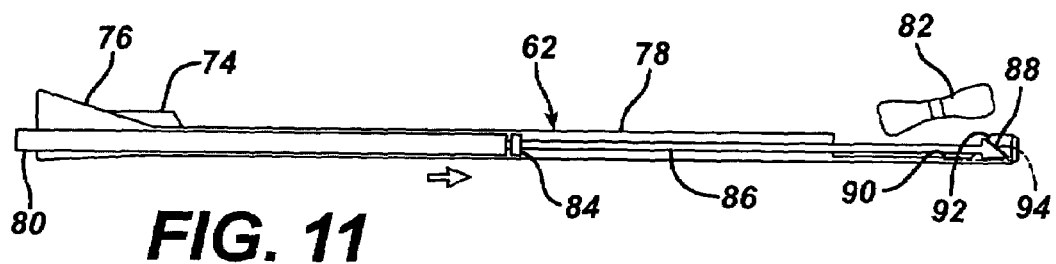
Figure 12:
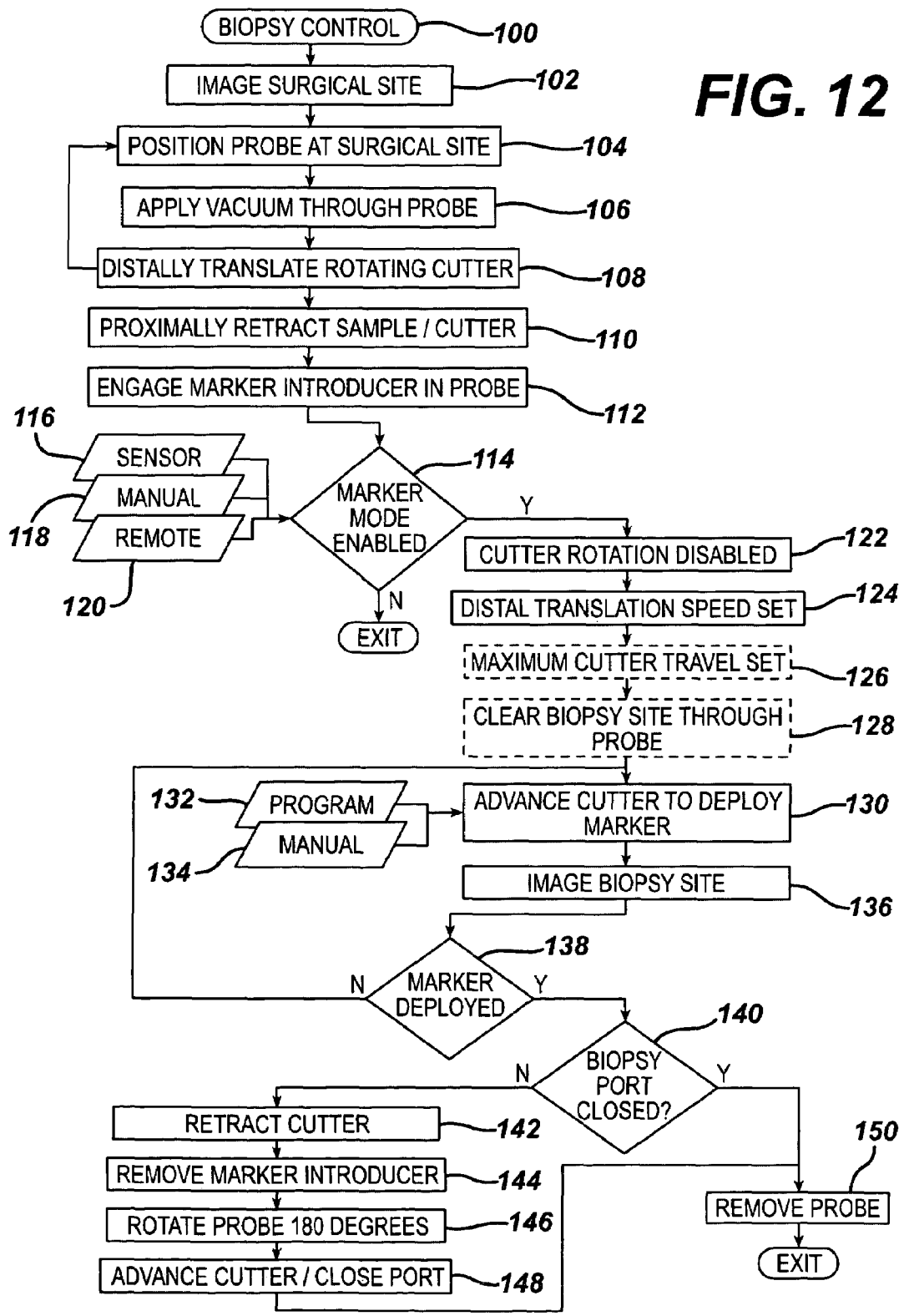
FIG. 12 is a sequence of operations or procedures for controlling a biopsy system to deploy a biopsy marker at a surgical biopsy site.

In FIG. 7, the marker introducing assembly 62 has been inserted into the probe 68 in preparation for the surgeon initiating deployment of the marker 82. In FIG. 8, the cutter 80 has been advanced into contact with a cutter seat 84. In FIG. 9, the cutter 80 has further distally advanced, driving a pusher rod 86 and its driving tip 88, and thus the distally placed marker 82 to expose the marker in a distal opening 90 of the introducer tube 78. In FIG. 10, the cutter 80 has been further advanced so that the distal end of the marker 82 ramps outward against an angled surface 92 of the distal opening 90. In FIG. 11, the cutter 80 has further advanced so that the driving tip 88 has underrun the fully deployed marker 82 and has been received within a tip slot 94 of the introducer tube 78 (shown also in FIG. 6).

The pusher rod 86 advantageously closes the distal opening 90 of the introduction assembly 62 and thus a specimen opening 96 of the probe 68. This may be an advantageous feature that allows retracting the probe 68 without inadvertently dragging out the marker 82. Thus, there is no requirement to rotate the probe 68 as an additional step or alternatively to remove the introduction assembly 62 and replace it with a stylus (not shown) to close the probe 68.

It is desirable to include a marker deployment mode into the controls of the biopsy system 12 to optimize this function. For instance, if two motors are used, one for longitudinal translation of the cutter and one for rotating the cutter 16, then dedicated control logic would allow disabling cutter rotation during deployment. Also, the amount of longitudinal travel and the rate of travel may be optimized for marker deployment. In FIG. 5, an illustrative sequence of operations or procedure 100 for biopsy device control of marker deployment is depicted as a flow diagram.

A surgical cite within the patient's breast is imaged (e.g., ultrasonic imaging) (block 102) to guide the surgeon to insert and position the probe (block 104). Vacuum is applied through the probe to assist in drawing tissue into a specimen bowl of the probe (block 106) while the cutter is rotated and distally translated to cut the tissue. The probe may be repositioned, such as by rotating the probe to present the specimen bowl at a different angle with the specimen bowl blocked by the extended cutter. Thereafter, the cutter and sample are proximally retracted (block 110). These actions of blocks 104-108 may be repeated to the surgical site between biopsies or by otherwise repositioning the probe.

Once the biopsies at the surgical site are complete, then the surgeon engages the marker introduction assembly ("introducer") into the biopsy probe (block 112) and enables deployment mode of the marker (block 114). The interface between the introducer and the biopsy handle may be such that its presence is sensed by a sensor (block 116) and automatically prepares the biopsy system for deployment mode, preventing inadvertent rotation of the cutter or an inappropriate application of the vacuum assist system and/or adjusting cutter travel and/or rate of travel. Enabling deployment mode may be manual (block 118) wherein the surgeon uses a control, such as pushing a deployment soft button, to initiate deployment mode. As a further example, a remote control unit that is spaced away from the biopsy handle may initiate deployment mode (block 120). For example, a control unit may be elsewhere in the surgical suite, for instance in an MRI or CTI facility wherein the biopsy system is remotely actuated.

If marker deployment mode has been enabled, then cutter rotation may advantageously be disabled in a two-motor biopsy system (block 122). Distal translation speed is set (block 124). For instance, a greater rate of travel may be desired to better propel the marker from the probe. Maximum cutter travel may be set (block 126) to avoid binding and damage, especially if the mechanical advantage of the motor and mechanization is such as to cause damage before full travel may be sensed. It may be desirable to use a fluid drainage capability of the biopsy system at this point, such as using the vacuum assist system to remove fluid from the surgical site and/or to insufflate the surgical site to provide a cavity to receive the biopsy marker (block 128).

Then the cutter is advanced to deploy the marker (block 130), which may be a programmed mode that is initiated by the surgeon (block 132) or a manual process (block 134) with a deployment command maintained by the surgeon. Imaging may be performed contemporaneously or subsequently to confirm that the marker has been deployed at the surgical site (block 136). Advancement continues until a determination is made that the marker is deployed (block 138), which may be determined based on one or more conditions such as the biopsy system sensing full travel, sensing of cutter binding at full travel, visual confirmation of the marker deployment, etc.

In some applications, the introducer and/or biopsy probe may be determined to be insufficiently closed at this point (block 140), such as the introducer prevents closure. To prevent inadvertently dislodging the marker, the cutter is retracted (block 142), the marker introducer is removed with the probe still in place (block 144), the probe is rotated (e.g., 180 degrees) so that the specimen bowl is moved away from the marker to prevent its inadvertent entry (block 146), and the cutter is advanced to close the port (block 148). Once the port is determined to be closed in blocks 140 or 148, then the probe is removed (block 150).

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, It should be appreciated that the illustrative embodiment describes a handheld biopsy procedure guided by ultrasonic imaging to accentuate advantages of incorporating marker placement into biopsy instrument controls. However, aspects of the present invention pertain to tabletop fixed biopsy instruments, biopsy instruments used for tissue other than the breast, biopsy instruments positioned with other imaging modalities such as X-ray and Magnetic Resonance Imaging (MRI), and remotely actuated biopsy instruments.

For example, although a vacuum-assisted biopsy system has been advantageously depicted herein as benefiting from a marker introduction device, it should be appreciated that application of a marker introduction device to a core needle biopsy device would provide similar advantages, allowing a surgeon to place a marker while positioning the core needle device with reference to a diagnostic image.

For another example, although a specific handheld biopsy device is described, it should be appreciated that a detachable probe may be used in conjunction with a marker introduction device.

As yet another example, although affirmatively driving the marker with the cutter of a biopsy handle has a number of advantages, it should be appreciated that the vacuum assist control system of a biopsy system consistent with aspects of the invention may be used to draw a plunger of a biopsy marker introduction device toward the distal end of the probe. With the plunger fully translated distally, the marker would deploy and then the vacuum assist may be removed, leaving the marker in place as the biopsy probe is removed.

What is claimed is:

1. A method of deployment of a biopsy marker at a biopsy surgical site within a body by use of a biopsy device, the method comprising:
providing a biopsy device including
a probe defining a cutter lumen having proximal and distal openings, and
a hollow cutter configured to be distally advanceable and proximally retractable through the cutter lumen, wherein the cutter is generally tubular,
wherein the cutter has a sharp open distal end configured to sever tissue;
advancing the cutter through the cutter lumen to sever a tissue sample with the sharp open distal end of the cutter;
retracting the cutter to expose the proximal opening of the cutter lumen;
providing a biopsy marker introduction assembly comprising an introducer tube, a marker disposed in the introducer tube, and a marker deployment rod disposed for translation within the introducer tube, the marker deployment rod having trailing and leading ends and a cutter seat portion proximate to the trailing end, configured to abut with the sharp open distal end of the cutter, the cutter seat having a diameter greater than that of the cutter;
inserting the biopsy marker introduction assembly into the proximal opening of the cutter lumen;
bringing the sharp open distal end of the cutter and the cutter seat portion of the marker deployment rod into abutment; and
distally advancing the cutter to drive the marker deployment rod and thus the marker to cause deployment of the marker through the distal opening of the cutter lumen at the biopsy surgical site.

2. The method of claim 1, wherein a distal portion of the cutter lumen communicates with a pneumatic source, the method further comprising:
insufflating the biopsy surgical site with the pneumatic source.

3. The method of claim 1, further comprising:
forming a pneumatic seal between the marker deployment rod and the introducer tube, wherein distally advancing the cutter forms a syringe pressure proximally to the pneumatic seal.

4. The method of claim 1 further comprising:
forming a pneumatic seal between the marker deployment rod and the introducer tube; and
forming a vacuum assist pressure in a distal portion of the cutter lumen, thereby distally drawing the marker deployment rod to deploy the marker.

5. The method of claim 1, further comprising proximally extending the marker deployment rod from the cutter lumen wherein distally advancing the cutter deploys the marker as the cutter approaches the cutter lumen.

6. The method of claim 1, further comprising distally advancing the cutter to position the marker deployment rod across a distal lateral opening in the biopsy probe enabling retraction of the biopsy probe without disturbing the deployed marker.

7. The method of claim 1, further comprising percutaneously deploying the marker during a core needle biopsy procedure.

8. A biopsy marker introduction device for deploying a biopsy marker through a biopsy instrument having a probe defining a cutter lumen including a probe lateral distal opening and a probe proximal opening, and a hollow cutter distally advanceable and proximally retractable through the cuter lumen, wherein the cutter has a sharp open distal end configured to sever tissue, the biopsy marker introduction device comprising:
an introducer tube configured to be received in the cutter lumen and having a tube lateral distal opening;

a marker slidingly received in the introducer tube; and a marker deployment rod at least partially disposed in the introducer tube proximal to the marker and slidingly received in the introducer tube, the marker deployment rod having a cutter seat configured for abutment with the sharp open distal end of the cutter to deploy the marker through the tube lateral distal opening, wherein the introducer tube and the tube lateral distal opening are configured such that when the introducer tube is inserted into the cutter lumen, the tube lateral distal opening and the probe lateral distal opening can be aligned at least in part, and wherein the marker deployment rod has a length adapted for cooperation with the cutter such that when the tube, marker and marker deployment rod are inserted into the cutter lumen, distally advancing the cutter will drive the marker deployment rod and cause the marker to be urged through the tube lateral distal opening and the probe lateral distal opening.

9. The device of claim 8, further comprising a proximal collar attached proximally to the introducer tube and configured for manipulating the device into the cuter lumen.

10. The device of claim 8, further comprising an alignment feature configured to rotationally orient the tube in the cutter lumen.

11. The device of claim 8, further comprising a pneumatic sealing feature dynamically sealing the marker deployment rod to the tube.

12. The device of claim 9, wherein the tube distally includes a deployment opening, the device further comprising a removable sealing tip engageable over the deployment opening.

13. The device of claim 8, wherein the distal opening includes a ramped surface to rampingly eject a distal end of the marker.

14. The device of claim 13, wherein the marker deployment rod distally terminates in a driving surface for rampingly ejecting a proximal end of the marker.

15. The device of claim 8, wherein at least a portion of the tube and marker deployment rod comprise a resilient material for flexibly inserting the device into the biopsy instrument.

16. A biopsy system for obtaining a biopsy sample, the biopsy system comprising:

a biopsy probe including a cutter lumen that communicates between a probe lateral distal opening and a probe proximal opening;

a biopsy handle holding the biopsy probe, having an actuator for cutting the biopsy sample through the biopsy probe;

a hollow cutter operably connected to the actuator, and distally advanceable and proximally retractable through the cutter lumen, wherein the cutter has a sharp open distal end configured to sever tissue; and a marker introduction device comprising:

an introducer tube configured to be received in the cutter lumen and having a tube lateral distal opening, a marker slidingly received in the tube, and a pusher proximal to the marker and slidingly received in the tube, and having a proximal cutter seat having a diameter greater than that of the cutter, the cutter seat configured for abutment with the sharp open distal end of the cutter;

wherein the introducer tube and the tube lateral distal opening are configured such that when the tube is inserted into the cutter lumen, the tube lateral distal opening and the probe lateral distal opening can be aligned at least in part, and wherein the pusher has a length adapted for cooperation with the cutter such that when the tube, marker and pusher are inserted into the cutter lumen, distally advancing the cutter will drive the pusher and cause the marker to be urged through the tube lateral distal opening and the probe lateral distal opening.

17. The biopsy system of claim 16, wherein the pusher is operably configured to dynamically seal to the tube, the biopsy system further comprising a vacuum assist system communicating pneumatically with a distal portion of the probe to assist in marker deployment.

18. The biopsy system of claim 17, wherein the vacuum assist system is operably configured to insufflate a surgical site.

19. The biopsy system of claim 17, wherein the vacuum assist system is operably configured to distally draw the pusher to deploy the marker.

20. The biopsy system of claim 16, wherein the pusher is operably configured to close the distal opening in the biopsy probe subsequent to marker deployment.

* * * * *